US005646160A

United States Patent [19]

Morris et al.

[11] Patent Number: 5,646,160
[45] Date of Patent: *Jul. 8, 1997

[54] METHOD OF TREATING HYPERPROLIFERATIVE VASCULAR DISEASE WITH RAPAMYCIN AND MYCOPHENOLIC ACID

[75] Inventors: Randall Ellis Morris, Los Altos; Clare Robert Gregory, Menlo Park, both of Calif.

[73] Assignee: American Home Products Corporation, Madison, N.J.

[*] Notice: The term of this patent shall not extend beyond the expiration date of Pat. No. 5,516,781.

[21] Appl. No.: 452,049

[22] Filed: May 26, 1995

Related U.S. Application Data

[63] Continuation of Ser. No. 238,305, May 12, 1994, Pat. No. 5,516,781, which is a continuation-in-part of Ser. No. 980,000, Nov. 23, 1992, abandoned, which is a continuation of Ser. No. 819,314, Jan. 9, 1992, abandoned.

[51] Int. Cl.⁶ .................. A61K 31/345; A61K 31/35
[52] U.S. Cl. .................. 514/291; 514/458; 514/456; 424/122
[58] Field of Search .................. 424/122; 514/291, 514/458, 456

[56] References Cited

U.S. PATENT DOCUMENTS

| | | | |
|---|---|---|---|
| 3,929,992 | 12/1975 | Sehgal et al. | 435/128 |
| 4,885,171 | 12/1989 | Surendra et al. | 424/122 |
| 5,078,999 | 1/1992 | Warner et al. | 424/122 |
| 5,080,899 | 1/1992 | Sturm et al. | 424/122 |
| 5,100,899 | 3/1992 | Calne | 514/291 |
| 5,252,579 | 10/1993 | Skofnicki | 514/291 |
| 5,256,790 | 10/1993 | Nelson | 514/291 |
| 5,283,257 | 2/1994 | Gregory et al. | 514/458 |
| 5,288,711 | 2/1994 | Mitchell et al. | 514/59 |

FOREIGN PATENT DOCUMENTS 0401747  6/1990  European Pat. Off. .

OTHER PUBLICATIONS

Gregory C.R., et al., American Society of Transplant Physicians, 13th Annual Meeting, May 16–18, 1994; Abstract (38) 9, mailed to attendees Apr. 27, 1994.
Gregory C.R., et al., American Society of Transplant Physicians, 13th Annual Meeting, May 16–18, 1994; Abstract (38) 10, mailed to attendees Apr. 27, 1994.
Gregory C.R., et al., Transplantation Proceedings, 25:1, 120–121 (Feb. 1993).
Gregory C.R., et al., Transplantation Proceedings, 25:1, 770–771 (Feb. 1993).
Gregory C.R., et al., Transplantation, 55:1409–1418 (Jun. 1993).
Gregory C.R., et al., Veterinary Surgery, Abstract 11:40 (Jan. 1993).
Gregory C.R. et al., J. Heart and Lung Transplantation, Abstract 27, 11:197 (1992).
Gregory C.R. et al., FASEB, Abstract 21, 6:A940 (1992).
Meiser, B.M. et al., J. Heart and Lung Transplantation, Abstract 3, 9:55 (1990).
Meiser, B.M. et al., Lancet 338:1297–1298 (1991).
Ferns, G.A. et al., Circulation, Abstract 0727, 80 (Supp. II) 183 (1989).
Jonasson, L. et al., Proc. Natl. Acad. Sci., 85:2303–2306 (Apr. 1988).
Morris, P.J. et al., Transplantation Reviews, 6:39 (1992)
Staruch, M.J., FASEB 3:3411 (1989).
Martel, R.R., Canadian Journal of Physiol. Pharmacology, 55:48 (1977).
Morris, R.E., Med. Sci. Res. 17:877 (1989).
Baeder, W.L., Fifth Int. Conf. Inflamm. Res. Assoc. 121 (Abstract)(1990) Eng, C.P. et al., The Journal of Antiboitics, 37:1231 (1984).
Commonly Owned U.S.S Patent Application Ser. No. 07/717,773 Filed Jun. 18, 1994.
The Merck Index, 9th ed., 6152:820–821 (1976).
Weaver, J.L., J. Cell Biology, Abstract 1308, 111:(5 Part 2)234a. Transplantation Proc. 23:2833 (1991).
Cytokine 3:472 (1991).
Transplantation Proc. 23:507 (1991).
Transplantation 50:554 (1990).
Ferns, G., Am. J. Path. 137:403 (1990).
Immunology 72:544 (1991).
Transplantation Proc. 23:2833 (1991).

*Primary Examiner*—Jean C. Witz
*Attorney, Agent, or Firm*—Arnold S. Milowsky

[57] ABSTRACT

This invention provides a method of preventing or treating hyperproliferative vascular disease in a mammal by administering an antiproliferative effective amount of rapamycin alone or in combination with mycophenolic acid.

11 Claims, No Drawings

METHOD OF TREATING HYPERPROLIFERATIVE VASCULAR DISEASE WITH RAPAMYCIN AND MYCOPHENOLIC ACID

CROSS REFERENCE TO RELATED APPLICATIONS

This is a continuation of application Ser. No. 08/238,305 filed May 12, 1994, now U.S. Pat. No. 5,516,781which is a continuation-in-part of U.S. Ser. No. 07/980,000 filed Nov. 23, 1992, now abandoned, which is a continuation of U.S. Ser. No. 07/819,314 filed Jan. 9, 1992, now abandoned.

BACKGROUND OF THE INVENTION

Many individuals suffer from heart disease caused by a partial blockage of the blood vessels that supply the heart with nutrients. More severe blockage of blood vessels in such individuals often leads to hypertension, ischemic injury, stroke, or myocardial infarction. Typically vascular occlusion is preceded by vascular stenosis resulting from intimal smooth muscle cell hyperplasia. The underlying cause of the intimal smooth muscle cell hyperplasia is vascular smooth muscle injury and disruption of the integrity of the endothelial lining. The overall disease process can be termed a hyperproliferative vascular disease because of the etiology of the disease process. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and cytokines that result in the smooth muscle cell proliferation and migration. T-cells and macrophages also migrate into the neointima. [Haudenschild, C., *Lab. Invest.* 41:407 (1979); Clowes, A., *Circ. Res.* 56:139 (1985); Clowes, A., J, *Cardiovas. Pharm.* 14 (Suppl. 6): S12 (1989); Manderson, J., Arterio. 9:289 (1989); Forrester, J., *J. Am. Coll. Cardiol.* 17:758 (1991)]. This cascade of events is not limited to arterial injury, but also occurs following injury to veins and arterioles.

Vascular injury causing intimal thickening can be broadly categorized as being either biologically or mechanically induced. Artherosclerosis is one of the most commonly occurring forms of biologically mediated vascular injury leading to stenosis. The migration and proliferation of vascular smooth muscle plays a crucial role in the pathogenisis of artherosclerosis. Artherosclerotic lesions include massive accumulation of lipid laden "foam cells" derived from monocyte/macrophage and smooth muscle cells. Formation of "foam cell" regions is associated with a breech of endothelial integrity and basal lamina destruction. Triggered by these events, restenosis is produced by a rapid and selective proliferation of vascular smooth muscle cells with increased new basal lamina (extracellular matrix) formation and results in eventual blocking of arterial pathways. [Davies, P. F., *Artherosclerosis Lab. Invest.* 55:5 (1986)].

Mechanical injuries leading to intimal thickening result following balloon angioplasty, vascular surgery, transplantation surgery, and other similar invasive processes that disrupt vascular integrity. Intimal thickening following balloon catheter injury has been studied in animals as a model for arterial restenosis that occurs in human patients following balloon angioplasty. Clowes, Ferns, Reidy and others have shown that deendothelilization with an intraartefial catheter that dilates an artery injures the innermost layers of roedial smooth muscle and may even kill some of the innermost cells. [Schwartz, S. M., *Human Pathology* 18:240 (1987); Fingerle, J., *Ateriosclerosis* 10:1082 (1990)]Injury is followed by a proliferation of the roedial smooth muscle cells, after which many of them migrate into the intima through fenestrae in the internal elastic lamina and proliferate to form a neointimal lesion.

Vascular stenosis can be detected and evaluated using angiographic or sonographic imaging techniques [Evans, R. G., *JAMA* 265:2382 (1991)]and is often treated by percutaneous transluminal coronary angioplasty (balloon catheterization). Within a few months following angioplasty, however, the blood flow is reduced in approximately 30–40 percent of these patients as a result of restenosis caused by a response to mechanical vascular injury suffered during the angioplasty procedure, as described above. [Pepine, C., *Circulation* 81:1753 (1990); Hardoff, R., *J. Am. Coll. Cardiol.* 15 1486 (1990)].

In an attempt to prevent restenosis or reduce intimal smooth muscle cell proliferation following angioplasty, numerous pharmaceutical agents have been employed clinically, concurrent with or following angioplasty. Most pharmaceutical agents employed in an attempt to prevent or reduce the extent of restenosis have been unsuccessful. The following list identifies several of the agents for which favorable clinical results have been reported: lovastatin [Sahni, R., *Circulation* 80 (Suppl.) 65 (1989); Gellman, J., *J. Am. Coll. Cardiol.* 17:251 (1991)]; thromboxane $A_2$synthetase inhibitors such as DP-1904 [Yabe.,Y., *Circulation* 80 (Suppl.) 260 (1989)]; eicosapentanoic acid [Nye, E., *Aust. N. Z. J. Med.* 20:549 (1990)]; ciprostene (a prostacyclin analog) [Demke, D., *Brit. J. Haematol* 76 (Suppl.): 20 (1990); Darius, H., *Eur. Heart J.* 12 (Suppl.): 26 (1991)]; trapidil (a platelet derived growth factor) [Okamoto, S., *Circulation* 82 (Suppl.): 428 (1990)]; angiotensin converting enzyme inhibitors [Gottlieb, N., *J. Am. Coll. Cardiol.* 17 (Suppl. A): 18 1A (1991)]; and low molecular weight heparin [de Vries, C., Eur. Heart J. 12 (Suppl.): 386 (1991)].

In an attempt to develop better agents for preventing or reducing smooth muscle proliferation and intimal thickening, the use of balloon catheter induced arterial injury in a variety of mammals has been developed as a standard model of vascular injury that will lead to intimal thickening and eventual vascular narrowing. [Chevru, A., *Surg. Gynecol. Obstet.* 171:443 (1990); Fishman, J., *Lab. Invest.* 32:339 (1975); Haudenschild, C., *Lab. Invest.* 41:407 (1979); Clowes, A. W., *Lab. Invest.* 49:208 (1983); Clowes, A. W., *J. Cardiovas. Pharm.* 14:S12 (1989); and Ferns, G. A., *Science* 253:1129 (1991)]. Many compounds have been evaluated in this standard animal model. The immunosuppressive agent cyclosporin A has been evaluated and has produced conflicting results. Jonasson reported that cyclosporin A caused an inhibition of the intimal proliferative lesion following arterial balloon catheterization in vivo, but did not inhibit smooth muscle cell proliferation in vitro. [Jonasson, L., *Proc. Natl. Acad. Sci.* 85:2303 (1988)]. Ferns, however reported that when deendothelilized rabbits were treated with cyclosporin A, no significant reduction of intimal proliferation was observed in vivo. Additionally, intimal accumulations of foamy macrophages, together with a number of vacuolated smooth muscle cells in the region adjacent to the internal elastic lamina were observed, indicating that cyclosporin A may modify and enhance lesions that form at the sites of arterial injury. [Ferns, G. A., *Circulation* 80 (Supp): 184 (1989); Ferns, G., *Am. J. Path.* 137:403 (1990)].

Rapamycin, a macrocyclic triene antibiotic produced by *Streptomyces hygroscopicus* [U.S. Pat. No. 3,929,992]has been shown to prevent the formation of humoral (IgE-like) antibodies in response to an albumin allergic challenge [Martel, R., *Can. J. Physiol. Pharm.* 55:48 (1977)], inhibit murine T-cell activation [Staruch, M., *FASEB* 3:3411 (1989) ], prolong survival time of organ grafts in histoincompatible rodents [Morris, R., *Med. Sci. Res.* 17:877 (1989)], and inhibit transplantation rejection in mammals [Calne, R., European Patent Application 401,747]. Rapamycin blocks calcium-dependent, calcium-independent, cytokine-independent and constitutive T and B cell division at the G1-S interface. Rapamycin inhibits gamma-interferon production induced by II-1 and also inhibits the gamma-interferon induced expression of membrane antigen. [Morris, R. E., *Transplantation Rev.* 6:39 (1992)]. The use of rapamycin in preventing coronary graft atherosclerosis (CGA) in rats has been disclosed by Meiser [*J. Heart Lung Transplant* 9:55 (1990)]. Arterial thickening following transplantation, known as CGA, is a limiting factor in graft survival that is caused by a chronic immunological response to the transplanted blood vessels by the transplant recipient's immune system. [Dec. G, *Transplantation Proc.* 23:2095 (1991) and Dunn, M. *Lancet* 339:1566 (1992)]. The disclosed invention is distinct from the use of rapamycin for preventing CGA, in that CGA does not involve injury to the recipients own blood vessels; it is a rejection type response. The disclosed invention is related to vascular injury to native blood vessels. The resulting intimal smooth muscle cell proliferation dose not involve the immune system, but is growth factor mediated. For example, arterial intimal thickening after balloon catheter injury is believed to be caused by growth factor (PGDF, bFGF, TGFb, IL-1 and others)-induced smooth muscle cell proliferation and migration. [Ip, J. H., *J. Am. Coll. Cardiol* 15:1667 (1990)]. Ferns has also shown that the immune response is not involved in arterial intimal thickening following balloon catheterization, as he found that there was no difference in intimal thickening between arteries from athymic nude rats (rats lacking T-cells) and normal rats after balloon catheterization [Am. J. Pathok 138:1045 (1991)].

DESCRIPTION OF THE INVENTION

This invention provides a method of preventing or treating hyperproliferative vascular disease in a mammal in need thereof by administering an antiproliferative effective amount of rapamycin to said mammal orally, parenterally, intravascularly, intranasally, intrabronchially, transdermally, rectally, or via a vascular stent impregnated with rapamycin.

As such, rapamycin is useful in treating intimal smooth muscle cell hyperplasia, restenosis, and vascular occlusion in a mammal, particularly following either biologically or mechanically mediated vascular injury, or under conditions that would predispose a mammal to suffering such a vascular injury. Biologically mediated vascular injury includes, but is not limited to injury attributed to infectious disorders including endotoxins and herpes viruses such as cytomegalovirus; metabolic disorders such as atherosclerosis; and vascular injury resulting from hypothermia, and irradiation. Mechanically mediated vascular injury includes, but is not limited to vascular injury caused by catheterization procedures or vascular scraping procedures such as percutaneous transluminal coronary angioplasty; vascular surgery; transplantation surgery; laser treatment; and other invasive procedures which disrupt the integrity of the vascular intima or endothelium. Rapamycin is also useful in preventing intimal smooth muscle cell hyperplasia, restenosis, and vascular occlusion resulting from mechanically mediated injury. In particular, for the prevention of restenosis following a percutaneous transluminal coronary angioplasty procedure.

Treating includes retarding the progression, arresting the development, as well as palliation. Preventing includes inhibiting the development of and prophylacticly preventing of hyperproliferative vascular disease in a susceptible mammal.

This invention also provides a method of using a combination of rapamycin and mycophenolic acid for the same utilities described above. Mycophenolic acid, an antiproliferative antimetabolite, inhibits inosine monophosphate dehydrogenase and guanosine monophosphate synthetase, enzymes in the de novo purine biosynthetic pathway. This results in an inhibition of DNA synthesis which causes an accumulation of cells at the G 1-S interface. Other combinations containing rapamycin that are useful for preventing or treating hyperproliferative vascular disease will be apparent to one skilled in the art. These include, but are not limited to, using rapamycin in combination with other anhproliferative antimetabolites.

The effect of rapamycin on hyperproliferative vascular disease was established in an in vitro and an in vivo standard pharmacological test procedure that emulates the hyperproliferative effects observed in mammals that are undergoing intimal smooth muscle proliferation and are therefore developing restenosis. Cycloporin A was also evaluated in these test procedures for the purpose of comparison. The combination of rapamycin and mycophenolic acid was evaluated in the in vivo test procedure. The procedures and the results obtained are described below.

Rapamycin and cyclosporin A were evaluated in an in vitro standard pharmacological test procedure which emulates the intimal smooth muscle cell proliferation observed following vascular injury. Results were obtained by measuring DNA and protein synthesis in rat smooth muscle cells that have been stimulated with a growth factor such as fetal calf serum or a hypertrophic mitogen, such as angiotensin II. The following briefly describes the procedure that was used. Rat smooth muscle cells were maintained in a 1:1 mixture of defined Eagle's medium (DEM) and Ham's F12 medium with 10% fetal calf serum, peniciliin (100 U/mL), streptomycin (100 mg/mL) and 25 mL Hepes at pH 7.4. Cells were incubated at 37° C. in a humidified atmosphere of 5% $CO_2$ with media changes every 2–3 days. Each compound tested was diluted with an appropriate vehicle to obtain a 1 mM stock solution. Ethanol was used as the vehicle for rapamycin and 20% tween 80 in ethanol was the vehicle for cyclosporin A. Test concentrations of drug were obtained by diluting appropriate concentrations of stock solution with serum free media. The smooth muscle cell culture was maintained in a defined serum free media containing 1:1 DEM and Ham's F12 medium, insulin ($5 \times 10^{-7}$M), transfertin (5 µg/mL), and ascorbate (0.2 mM) for 72 hours before testing in a multi-well plate. After the 72 hour period, an appropriate quantity of stock solution containing either rapamycin or cyclosporin A was added to the smooth muscle cell culture and media mixture. After a 24 hours the appropriate growth factor was added. For the measurement of DNA synthesis, $^3$H-thymidine was added at 12 hours after the growth factor was added, and the cells were harvested at 36 hours. For the measurement of protein synthesis, $^3$H-leucine was added at 14 hours after the growth factor was added, and the cells were harvested at 18 hours. The amount of incorporated radioactive label was measured on a scintillation counter.

The following table shows the results obtained for rapamycin on DNA and protein synthesis in smooth muscle cells that were stimulated with 10% fetal calf serum, as measured by incorporation of tritiated thymidine or leucine into smooth muscle cells. The mount of tritiated label incorporated by the smooth muscle cells that were treated with media only was normalized to 100%, and the results for cells treated with fetal calf serum or fetal calf serum plus the test compound are expressed as a percent comparison with the cells treated with media only.

| EFFECT OF RAPAMYCIN ON DNA AND PROTEIN SYNTHESIS IN SMOOTH CELLS STIMULATED WITH FETAL CALF SERUM* | | |
|---|---|---|
| | $^3$H-Thymidine Incorporation (% of Media) | $^3$H-Leucine Incorporation (% of Media) |
| Media | 100% | 100% |
| FCS | 495% | 174% |
| 1000 nM RAP + FCS | 136% | 95% |
| 100 nM RAP + FCS | 172% | 91% |
| 10 nM RAP + FCS | 204% | 74% |
| 1 nM RAP + FCS | 403% | 106% |

*Abbreviations: RAP = rapamycin; Media = defined serum free media; and FCS = 10% fetal calf serum.

The following table shows the results obtained for rapamycin on protein synthesis in smooth muscle cells that were stimulated with $10^6$ nM angiotensin II, as measured by incorporation of tritiated leucine into smooth muscle cells. The amount of tritiated label incorporated by the smooth muscle cells that were treated with media only were normalized to 100%, and the results for cells treated with angiotensin or angiotensin plus the test compound are expressed as a percent comparison with the cells treated with media only.

| EFFECT OF RAPAMYCIN ON PROTEIN SYNTHESIS IN SMOOTH CELLS STIMULATED WITH ANGIOTENSIN II* | |
|---|---|
| | $^3$H-Leucine Incorporation (% of Media) |
| Media | 100% |
| ANG | 159% |
| 1000 nM RAP + ANG | 53% |
| 100 nM RAP + ANG | 57% |
| 10 nM RAP + ANG | 61% |
| 1 nM RAP + ANG | 60% |

*Abbreviations: RAP = rapamycin; Media = defined serum free media; and ANG = $10^{-6}$ nM angiotensin II.

The results of the standard in vitro test procedure showed that rapamycin had a pronounced antiproliferative effect in the presence of FCS and an anti-hypertrophic effect in the presence of angiotensin II. Following vascular injury, DNA and protein synthesis of smooth muscle cells are necessary for the development of restenosis to occur. These results showed that rapamycin inhibited both DNA and protein synthesis in stimulated smooth muscle cells. An antiproliferative effect was also observed with cyclosporin A; however, at 1000 nM, cyclosporin A was cytotoxic and not merely cytostatic. At 1000 nM, cyclosporin A caused lysis of the smooth muscle cells as evidenced by the presence of lactic acid dehydrogenase in the supernalant of the cell culture. Similar toxicity to smooth muscle cells was not observed for rapamycin.

Rapamycin, rapamycin plus mycophenolic acid, and cyclosporin A were evaluated in an in vivo standard pharmacological test procedure that emulates the vascular injury suffered and restenosis that develops following percutaneous transluminal coronary angioplasty in humans. The ability of a test compound to inhibit restenosis was determined by comparing intimal thickening in mammals treated with test compound following balloon catheterization versus intimal thickening in untreated control mammals after the same test procedure. [Chevru, A., Surg. Gynecol. Obstet. 443 (1990); Fishman, J., Lab. Invest. 32:339 (1975); Haudenschild, C., Lab. Invest. 41:407 (1979); Clowes, A. W., Lab. Invest. 49:208 (1983); Clowes, A. W., J. Cardiovas. Pharm. 14:S12 (1989); and Ferns, G. A., Science 253:1129 (1991)]. The following briefly describes the procedure that was used. The left carotid arteries of male Sprague-Dawley rats were injured with an inflated 2Fr balloon catheter. During a 14 day postoperative period, these rats were divided into groups and treated daily with rapamycin (1.5 mg/kg; i.p.), rapamycin plus mycophenolic acid (1.5 mg/kg; i.p.+40 mg/kg; p.o.), or cyclosporin A (3 mg/kg; i.p.). Treatment was administered on days 0 to 13 postoperatively. Additionally, one group each also received rapamycin (6 mg/kg/day; i.p.) or cyclospodn A (40 mg/kg/day; i.p.) for two days postoperatively, and then received no treatment for the next 12 days. An untreated group was used an injured control to establish the amount of intimal growth in the absence of treatment. The right carotid was used as an uninjured control in all groups. After the 14-day period, the rats were sacrificed, the carotids removed. The mean areas of the intima and blood vessel wall were measured by morphometry. Results are expressed as an intima percent which can be expressed according to the following formula:

$$\frac{\text{area of intima}}{\text{area of vessel}} * 100$$

The following table shows the results that were obtained.

| EFFECT OF RAPAMYCIN ON INTIMAL THICKENING IN INJURED CAROTID ARTERIES (DAY 14)* | |
|---|---|
| Test Group | Intima Percent ± S.E. |
| Uninjured Control | 0.00 ± 0.00 |
| Untreated Injured Control | 33.3 ± 19.66 |
| RAP (1.5 mg/kg - 14 days) | 6.78 ± 4.69 |
| RAP (6 mg/kg - 2 days) | 16.56 ± 6.22 |
| RAP + MPA (14 days) | 1.6 ± 3.5 |
| CsA (3 mg/kg - 14 days) | 26.46 ± 27.42 |
| CsA (40 mg/kg - 2 days) | 31.14 ± 20.66 |

*Abbreviations RAP = rapamycin; MPA = mycophenolic acid; and CsA = cyclosporin A.

These results show that treatment with rapamycin (1.5 mg/kg for 14 days) resulted in an 80% decrease in the mean percentage intimal thickening compared with the untreated injured control group. Similarly, treatment with the combination of rapamycin and mycophenolic acid produced almost a complete inhibition of intimal thickening (95% reduction in intimal thickening compared with untreated injured control). Cyclosporin A failed to produce any meaningful reduction in intimal thickening.

Similar results were obtained when rapamycin was evaluated at different doses in the above in vivo standard pharmacological test procedure that emulates the vascular injury that occurs following a percutaneous transluminal coronary angioplasty procedure in humans. Rapamycin was administered on postoperative days 0–13, and examination by morphometry was performed on day 14. Rapamycin, at a dose of 1.5 and 3 mg/kg significantly arrested the development of restenosis as measured by the intima percent 14 days after balloon catheterization, whereas restenosis was clearly observed in the untreated injured control group. These results are summarized in the table below.

EFFECT OF RAPAMYCIN ON INTIMAL THICKENING IN INJURED CAROTID ARTERIES (DAY 14)

| Group | Dose | Treatment Days | Intima Percent ± S.E. |
|---|---|---|---|
| Uninjured Control | | | 0.00 ± 0.00 |
| Untreated Injured Control | | | 44.51 ± 5.03 |
| Rapamycin | 6 mg/kg | 0–13 | 30.92 ± 4.06 |
| Rapamycin | 3 mg/kg | 0–13 | 22.68 ± 6.28 |
| Rapamycin | 1.5 mg/kg | 0–13 | 21.89 ± 4.2 |

The results of the in vitro and in vivo standard test procedures demonstrate that rapamycin and rapamycin in combination with mycophenolic acid are useful in treating hyperproliferative vascular disease.

As such, rapamycin is useful in treating intimal smooth muscle cell hyperplasia, restenosis, and vascular occlusion in a mammal, particularly following either biologically or mechanically mediated vascular injury, or under conditions that would predispose a mammal to suffering such a vascular injury. Biologically mediated vascular injury includes, but is not limited to injury attributed to infectious disorders including endotoxins and herpes viruses such as cytomegalovirus; metabolic disorders such as atherosclerosis; and vascular injury resulting from hypothermia, and irradiation. Mechanically mediated vascular injury includes, but is not limited to vascular injury caused by catheterization procedures or vascular scraping procedures such as percutaneous transluminal coronary angioplasty; vascular surgery; transplantation surgery; laser treatment; and other invasive procedures which disrupt the integrity of the vascular intima or endothelium.

Rapamycin and rapamycin plus mycophenolic acid were also evaluated in a modification of the in vivo test procedure described above. In the modified test procedure, treatment with rapamycin or rapamycin plus mycophenolic acid were stopped on day 14, as above, but the animals were not sacrificed immediately. Intimal thickening was observed when the animals were sacrificed 1, 2, 4 weeks, and 44 days after treatment had been stopped. Microscopic analysis showed that endothelium regeneration had not occurred during the two week treatment period. For example, 44 days after undergoing balloon catheterization procedure of the carotid artery, untreated injured control rats had an intima percent (±S.E.) of 62.85+3.63, and rats treated with rapamycin+mycophenolic acid (1.5 /40 mg/kg) on postoperative days 0–13 had an intima percent (±S.E.) of 50.39+ 2.58. Better results were not obtained when the same regimen was administered on days 0–30 (intima percent (±S.E.) of 53.55±2.85). Following cessation of treatment with rapamycin or rapamycin plus mycophenolic acid intimal proliferation, that was previously suppressed, was able to occur. These results are consistent with the results shown in the table above, in which treatment for 2 days with rapamycin followed by 12 days of no treatment inhibited intimal thickening to a lesser degree than treatment with rapamycin for 14 days. These results are expected, as in the absence on an integral endothelial layer, the intimal smooth muscle cells will proliferate. It has been shown that intimal smooth muscle cell growth does not have an inhibitory effect on normal endothelial regeneration, and that intimal smooth muscle cell proliferation ceases when the endothelial layer is established. [Reidy, M., Lab. Invest. 59:36 (1988); Chevru, A., Surg. Gynecol. Obstet. 171:443 (1990); Fishman, J., Lab. Invest. 32:339 (1975); Haudenschild, C., Lab. Invest. 41:407 (1979)]. As such, treatment with rapamycin or rapamycin in combination with mycophenolic acid should be employed so long as the beneficial effect is seen. As the degree of restenosis can be monitored by angiographic and sonographic techniques, the dosage necessary to sustain the opened vessels can be adjusted.

To evaluate the ability of rapamycin and rapamycin plus mycophenolic acid to prevent restenosis following an angioplasty procedure, rapamycin was evaluated in the same in vivo standard pharmacological test procedure for restenosis that was described above, except that treatment with rapamycin began three days before (day -3) the angioplasty procedure was performed. The following table shows the results obtained on day 14 following balloon catheterization of the carotid artery on day 0. Results for treatment from day 3 to 13 are also provided.

EFFECT OF RAPAMYCIN ON INTIMAL THICKENING IN INJURED CAROTID ARTERIES (DAY 14)

| Group | Dose | Treatment Days | Intima Percent ± S.E. |
|---|---|---|---|
| Uninjured Control | | | 0.00 ± 0.00 |
| Untreated Injured Control | | | 44.51 ± 5.03 |
| Rapamycin | 1.5 mg/kg | −3–13* | 9.85 ± 1.15 |
| Rapamycin | 1.5 mg/kg | −3–3 | 30.7 ± 6.67 |
| Rapamycin | 1.5 mg/kg | −3–0 | 37.31 ± 4.33 |
| Rapamycin | 1.5 mg/kg | 3–13 | 44.38 ± 5.49 |

*Treatment from three days pre-balloon catheterization to day 13 days post-catheterization.

The results in the table above show that rapamycin prevented the development of restenosis following a balloon angioplasty procedure of the carotid artery, when rapamycin was administered from three days pre-angioplasty until day 13. Treatment from day minus 3 until day 3 or day 0 afforded a lesser degree of prevention, and treatment from day 3 to day 13 did not prevent restenosis.

The effect of rapamycin plus mycophenolic acid (MPA) was also evaluated in the angioplasty standard pharmacological test procedure. The table below shows the results obtained where rats underwent a balloon catheterization procedure of the carotid artery on day 0, and were sacrificed and examined morphometrically on day 44. The treatment regimen is described in the table.

EFFECT OF RAPAMYCIN + MPA ON INTIMAL THICKENING IN INJURED CAROTID ARTERIES (DAY 44)

| Group | Dose | Treatment Days | Intima Percent ± S.E. |
|---|---|---|---|
| Uninjured Control | | | 0.00 ± 0.00 |
| Untreated Injured Control | | | 62.85 ± 3.63 |
| Rapamycin + MPA | 40/1.5 mg/kg | 0–13 | 50.39 ± 2.58 |

EFFECT OF RAPAMYCIN + MPA ON INTIMAL
THICKENING IN INJURED CAROTID ARTERIES
(DAY 44)

| Group | Dose | Treatment Days | Intima Percent ± S.E. |
|---|---|---|---|
| Rapamycin + MPA | 40/1.5 mg/kg | 0–30 | 53.55 ± 2.85 |
| Rapamycin + MPA | 40/1.5 mg/kg | –3–13 | 18.76 ± 10.6 |

These results show that treatment with rapamycin and mycophenolic acid from day minus 3 to day 13 did effectively prevent restenosis at day 44, whereas the regimens which did not include drug administration before the angioplasty procedure did not effectively prevent restenosis at day 44.

Similar results were obtained when rat thoracic aortas were subjected to a balloon catheterization procedure, as described above, on day 0. The rats were either sacrificed and examined on day 14 or on day 44. The results obtained with rapamycin and rapamycin plus mycophenolic acid (MPA) are shown in the table below.

EFFECT OF RAPAMYCIN AND RAPAMYCIN +
MPA ON INTIMAL THICKENING IN INJURED
THORACIC AORTAS

| Group | Dose | Treatment Days | Intima Percent ± S.E. |
|---|---|---|---|
| Day 14 results | | | |
| Uninjured Control | | | 0.00 ± 0.00 |
| Untreated Injured Control | | | 15.52 ± 2.99 |
| Rapamycin + MPA | 40/1.5 mg/kg | –3–13 | 0.00 ± 0.00 |
| Day 44 Results | | | |
| Uninjured Control | | | 0.00 ± 0.00 |
| Untreated Injured Control | | | 28.76 ± 6.52 |
| Rapamycin | 1.5 mg/kg | –3–13 | 0.00 ± 0.00 |
| Rapamycin + MPA | 40/1.5 mg/kg | –3–13 | 8.76 ± 3.34 |

The results in the table above show that treatment with rapamycin from 3 days preoperatively until 13 days post-operatively completely prevented the development of restenosis 44 days after a balloon catheterization of the thoracic aorta. Using the same treatment regimen, rapamycin plus mycophenolic acid completely prevented restenosis 14 days after balloon catheterization and significantly prevented restenosis 44 days following balloon catheterization.

Similarly, day minus 3 to day 13 treatment with rapamycin plus mycophenolic acid completely prevented restenosis 14 days after balloon catheterizaton of the abdominal aortas in rats. These results are shown in the table below.

EFFECT OF RAPAMYCIN + MPA ON INTIMAL
THICKENING IN INJURED ABDOMINAL AORTAS
(DAY 14)

| Group | Dose | Treatment Days | Intima Percent ± S.E. |
|---|---|---|---|
| Uninjured Control | | | 0.00 ± 0.00 |
| Untreated Injured Control | | | 10.17 ± 2.42 |
| Rapamycin + MPA | 40/1.5 mg/kg | –3–13 | 0.00 ± 0.00 |

The results in the tables above show that rapamycin, alone or in combination with mycophenolic acid, is useful in preventing restenosis following invasive procedures that disrupt the vascular endothelial lining, such as percutaneous transluminal coronary angioplasty, vascular catheterization, vascular scraping, vascular surgery, or laser treatment procedures. These data also show that the administration of rapamycin, alone or in combination with mycophenolic acid, from 3 days pre-catheterization to 13 days post-catheterization, allowed the endothelium to heal, while preventing intimal smooth muscle cell proliferation. That intimal proliferation did not occur 31 days after administration with rapamycin, alone or in combination with mycophenolic acid, had been stopped, demonstrates that the endothelial layer had regenerated, as intimal proliferation stops after the reestablishment of the endothelial layer. The reestablishment of an intact endothelial layer was confirmed by microscopic examination of the previously catheterized arteries after removal at 44 days.

From the data above, it is particularly preferred that treatment begin with rapamycin or rapamycin plus mycophenolic acid before the procedure is performed, and that treatment should continue after the procedure has been performed. The length of treatment necessary to prevent restenosis will vary from patient to patient. For percutaneous transluminal angioplasty procedures, it is preferred that treatment be administered from 3 or more days before the procedure and continuing for 8 or more days after the procedure. It is more preferred that administration will be for 3 or more days before the angioplasty procedure and continuing for 13 or more days after the procedure. The same administration protocol is applicable when rapamycin, alone or in combination with mycophenolic acid, is used to prevent restenosis following vascular catheterization, vascular scraping, vascular surgery, or laser treatment procedures.

When rapamycin is employed alone or in combination with mycophenolic acid in the prevention or treatment of hyperproliferative vascular disease, it can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionaed coconut oil and arachis oil). For parenteral administration, the carrier can also be an oily ester such as ethyl oleate and isopropyl myristate. Sterile liquid carders are useful in sterile liquid form compositions for parenteral administration. The liquid carder for pressurized compositions can be halogenated, hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Rapamycin, alone or in combination with mycophenolic acid, may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. Rapamycin, alone or in combination with mycophenolic acid, may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

Rapamycin, alone or in combination with mycophenolic acid can be administered intravascularly or via a vascular stent impregnated with rapamycin, alone or in combination with mycophenolic acid, during balloon catheterization to provide localized effects immediately following injury.

Rapamycin, alone or in combination with mycophenolic acid, may be administered topically as a solution, cream, or lotion by formulation with pharmaceutically acceptable vehicles containing 0.1–5 percent, preferably 2%, of active compound.

The dosage requirements vary with the particular compositions employed, the route of administration, the severity of the symptoms presented and the particular subject being treated. Based on the results obtained in the standard pharmacological test procedures, projected daily intravenous dosages of rapamycin, when administered as the sole active compound or in combination with mycophenolic acid, would be 0.001–25 mg/kg, preferably between 0.005–10 mg/kg, and more preferably between 0.01–5 mg/kg. Projected daily oral dosages of rapamycin, when administered as the sole active compound or in combination with mycophenolic acid, would be 0.005–50 mg/kg, preferably between 0.01–25 mg/kg, and more preferably between 0.05–10 mg/kg. Projected daily intravenous dosages of mycophenolic acid, when used in combination with rapamycin, would be 0.5–75 mg/kg and preferably between 5–50 mg/kg. Projected daily oral dosages of mycophenolic acid, when used in combination with rapamycin, would be 1–75 mg/kg and preferably between 10–50 mg/kg.

Treatment will generally be initiated with small dosages less than the optimum dose of the compound. Thereafter the dosage is increased until the optimum effect under the circumstances is reached; precise dosages for oral, parenteral, intravascular, intranasal, intrabronchial, transdermal, or rectal administration will be determined by the administering physician based on experience with the individual subject treated. In general, rapamycin is most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of treating a hyperproliferative vascular disease selected from the group consisting of intimal smooth muscle cell proliferation, restenosis, and vascular occlusion, wherein the intimal smooth muscle cell proliferation, restenosis, or vascular occlusion is caused by an infectious disorder, a metabolic disorder, hypothermia, or irradiation, which comprises administering an antiproliferative effective amount of a combination of rapamycin and mycophenolic acid to said mammal orally, parenterally, intravascularly, intranasally, intrabronchially, transdermally, rectally, or via a vascular stent impregnated with rapamycin and mycophenolic acid.

2. A method of treating a hyperproliferative vascular disease selected from the group consisting of intimal smooth muscle cell proliferation, restenosis, and vascular occlusion, wherein the intimal smooth muscle cell proliferation, restenosis, or vascular occlusion is caused by vascular catheterization, vascular scraping, percutaneous transluminal coronary angioplasty, vascular surgery, or laser treatment, which comprises, administering an antiproliferative effective amount of a combination of rapamycin and mycophenolic acid to said mammal orally, parenterally, intravascularly, intranasally, intrabronchially, transdermally, rectally, or via a vascular stent impregnated with rapamycin and mycophenolic acid.

3. A method of treating restenosis in a mammal resulting from said mammal undergoing a percutaneous transluminal coronary angioplasty procedure which comprises administering an antirestenosis effective amount of a combination of rapamycin and mycophenolic acid to said mammal orally, parenterally intravascularly, intranasally, intrabronchially, transdermally, rectally, or via a vascular stent impregnated with rapamycin and mycophenolic acid.

4. A method of inhibiting restenosis in a mammal resulting from said mammal undergoing a percutaneous transluminal coronary angioplasty procedure which comprises administering an antirestenosis effective amount of a combination of rapamycin and mycophenolic acid to said mammal orally, parenterally intravascularly, intranasally, intrabronchially, transdermally, rectally, or via a vascular stent impregnated with rapamycin.

5. The method according to claim 4, wherein the administration of the combination of rapamycin and mycophenolic acid is initiated before the mammal undergoes the percutaneous transluminal coronary angioplasty procedure.

6. The method according to claim 5, wherein the combination of rapamycin and mycophenolic acid is administered for 3 or more days before the mammal undergoes the percutaneous transluminal coronary angioplasty procedure and said administration continues for 8 or more days following the percutaneous transluminal coronary angioplasty procedure.

7. The method according to claim 6, wherein the combination of rapamycin and mycophenolic acid is administered for 13 or more days following the percutaneous transluminal coronary angioplasty procedure.

8. A method of inhibiting restenosis in a mammal resulting from said mammal undergoing a undergoing a vascular catheterization, vascular scraping, vascular surgery, or laser treatment procedure which comprises administering an anti-restenosis effective amount of a combination of rapamycin and mycophenolic acid to said mammal orally, parenterally intravascularly, intranasally, intrabronchially, transdermally, rectally, or via a vascular stent impregnated with rapamycin and mycophenolic acid.

9. The method according to claim 8, wherein the administration of the combination of rapamycin and mycophenolic acid is initiated before the mammal undergoes the procedure.

10. The method according to claim 9, wherein the combination of rapamycin and mycophenolic acid is administered for 3 or more days before the mamma undergoes the percutaneous transluminal coronary angioplasty procedure and said administration continues for 8 or more days following the procedure.

11. The method according to claim 10, wherein the combination of rapamycin and mycophenolic acid is administered for 13 or more days following the procedure.

* * * * *